(12) United States Patent  
Tiryaki (10) Patent No.: US 11,306,285 B2  
(45) Date of Patent: Apr. 19, 2022

(54) ADIPOSE TISSUE SPLITTING KIT

(71) Applicant: Kemal Tunc Tiryaki, Istanbul (TR)

(72) Inventor: Kemal Tunc Tiryaki, Istanbul (TR)

( * ) Notice: Subject to any disclaimer, the term of this patent is extended or adjusted under 35 U.S.C. 154(b) by 194 days.

(21) Appl. No.: 16/610,752

(22) PCT Filed: Jul. 24, 2018

(86) PCT No.: PCT/TR2018/050396  
§ 371 (c)(1),  
(2) Date: Nov. 4, 2019

(87) PCT Pub. No.: WO2019/125324  
PCT Pub. Date: Jun. 27, 2019

(65) Prior Publication Data  
US 2020/0063087 A1    Feb. 27, 2020

(30) Foreign Application Priority Data  
Oct. 20, 2017 (TR) .......................... TR2017/16262

(51) Int. Cl.  
*C12M 1/33* (2006.01)  
*B26D 1/03* (2006.01)  
(Continued)

(52) U.S. Cl.  
CPC .............. *C12M 45/02* (2013.01); *B26D 1/03* (2013.01); *B26D 3/28* (2013.01); *B26D 7/0658* (2013.01);  
(Continued)

(58) Field of Classification Search  
CPC ...... C12M 45/02; C12M 23/34; C12M 27/14; C12M 33/04; B26D 1/03; B26D 7/0658  
See application file for complete search history.

(56) References Cited

U.S. PATENT DOCUMENTS 5,786,207 A * 7/1998 Katz ...................... C12M 45/02  
435/267  
9,575,055 B2 * 2/2017 Gevaert ................. C12M 35/08  
(Continued)

FOREIGN PATENT DOCUMENTS

WO    2009073724 A1    6/2009  
WO    2011117821 A1    9/2011

OTHER PUBLICATIONS

International Search Report for corresponding PCT/TR2018/050396.

*Primary Examiner* — Omar Flores Sanchez  
(74) *Attorney, Agent, or Firm* — Bayramoglu Law Offices LLC (57) ABSTRACT

The present invention is a kit to be used for obtaining Adipose tissue-based stem cells, which especially is suitable for obtainment of Adipose tissue-based stem cells, which comprises a reservoir (1) through which the entrance of the adipose tissue, that is taken from a predetermined area of the individual, into the kit; characterized by comprising a first housing (2), which is located on the said reservoir (1) and enables the transmission of the adipose tissue into the kit, a second housing (3), which is located on the said reservoir (1) and which enables the second injector (40) to be positioned outside the reservoir (1) and in a perpendicular position to the reservoir (1), a third housing (4) which enables the third injector (50) to be positioned outside the reservoir (1) and in a perpendicular position to the reservoir (1), an empty body (6) which is fixed inside the reservoir (1), a first inlet (7) which enables the transmission of the adipose tissue into the body (6) by pushing of the injector, a passage (8) which can rotate its own axis and which enables the circulation of the adipose tissue that is inside the body (6) between a desired inlet inside the body (6) and another inlet which is positioned in a 90 degree angle to this inlet by this rotation (Continued)

movement, at least one cover (10) which enables the said movement of the passage (8) and covers the top of the reservoir (1), a second inlet (12) which comprises a first splitting element (11) that is obtained by alignment of a multiple of cutting elements (10), and a third inlet (14) which comprises at least one second splitting element (13) which enables the adipose tissue split when it enters to and exits from the injector and is obtained by alignment of a multiple of cutting elements (10).

9 Claims, 4 Drawing Sheets

(51) Int. Cl.
- *B26D 3/28* (2006.01)
- *B26D 7/06* (2006.01)
- *C12M 1/00* (2006.01)
- *C12M 3/06* (2006.01)
- *C12M 1/26* (2006.01)

(52) U.S. Cl.
CPC ............ *C12M 23/34* (2013.01); *C12M 27/14* (2013.01); *C12M 33/04* (2013.01)

(56) References Cited

U.S. PATENT DOCUMENTS

| | | | |
|---|---|---|---|
| 10,702,629 B2* | 7/2020 | Pilkington | ............ B01D 17/047 |
| 2005/0058632 A1 | 3/2005 | Hedrick et al. | |
| 2013/0236970 A1* | 9/2013 | Anneren | ................ C12M 25/16 |
| | | | 435/380 |
| 2013/0344589 A1 | 12/2013 | Winkler et al. | |
| 2014/0080212 A1* | 3/2014 | Asgari | ................... C12M 21/08 |
| | | | 435/383 |
| 2014/0363891 A1 | 12/2014 | Llull et al. | |
| 2015/0218506 A1 | 8/2015 | Nash et al. | |
| 2016/0333305 A1 | 11/2016 | Pilkington et al. | |
| 2017/0205397 A1* | 7/2017 | Gevaert | ............. G01N 33/5029 |
| 2020/0088719 A1* | 3/2020 | Gevaert | ................ C12M 23/44 |

* cited by examiner

ADIPOSE TISSUE SPLITTING KIT

TECHNICAL FIELD

The invention relates to a kit which is developed for obtaining stem cells from adipose tissue that exists in the human body.

The invention specifically relates to a system which enables the mechanical isolation of stem cells from adipose tissue by using blades with different slopes and with the help of negative pressure inside a sterile closed box, without violating closed system conditions, by eliminating the obligation of using an enzyme, without a need for a laboratory medium, in order to obtain adipose-based stem cells.

PRIOR ART

Stem cells can be obtained from embryo, fetus, or bone marrow, blood, adipose etc. tissues that are in human body. The stem cells that exist in human body, unlike the embryonic stem cells, are pioneer tissue cells with the ability to transform into only specific tissue cells.

Currently, various methods of obtaining stem cells from adipose tissue are developed after the discovery that stems cells obtained from adipose tissue are efficient in repair of tissue damages and rejuvenation of the tissues. Accordingly, in the prior art, preferably; the adipose tissue that exists in the abdominal area or the upper part of legs of the individual are obtained with one of the liposuction methods that are known in prior art and are delivered to the laboratory. Adipose tissue sample is subjected to centrifuge process in order to eliminate the erythrocyte and alike materials on it and adipose tissue layer is obtained. Adipose tissue layer is drawn by a pipe and is subjected to enzyme, preferably collagenase enzyme, in a one to one ratio for one hour so that the adipose tissue is split and cells come out. With a second centrifuge process, the cells that are eluted precipitate and the supernatant part is disposed in order to obtain cell pellet. The obtained cell pellet is thawed with a solution in the desired ratio and the transplant is performed by the methods that fit to the individual. However, the greatest disadvantage in this method is that because the method is not applied in a laboratory medium; the said stem cells may lose their vitality during the time between obtaining the stem cells and transplanting them to the individual. In addition, the enzyme that is used in this method brings a financial burden as well as the process lasts longer since the effect of the said enzyme needs to be neutralized. Due to the abovementioned reasons, there is a need of developing a new method which enables obtaining adipose-based stem cells in a more practical manner and also performing this process in the medium which the adipose tissue is obtained.

In the patent document with number US2016333305, which sets an example for the prior art, a kit is described which splits the adipose cells and adjust their size in a desirable manner. In the said document, there is an inlet, an outlet, a passage that lies between the said inlet and the said outlet, at least two filtering elements that are located inside the said passage and has different apertures and a housing that seats onto the inlet and is suitable for the injector inlet. In the said process, the adipose tissue is taken inside the kit by injector and is tried to split by passing through the filtering elements located inside the passage. In the invention that is developed in the mentioned document, only the resizing the adipose cells into the desired size by splitting is described and no splitting process performed in an efficient manner between the adipose tissue and obtainment of stem cells is described. Therefore; a centrifuge process cannot be mentioned. The technical problem here is that there is not a possibility for the adipose tissue which passes through the injector can pass between the filtering elements more than once and therefore, the digestion cannot be completed in the desired manner. On the other hand, in our invention, the adipose tissue can be transferred repeatedly between 2 injectors, by being pulled by one and pushed by the other. In order for the desired digestion to be realized, the repetition of the process is very important. In addition to that, in the said system the adipose tissue passes though the filters by being pushed; however, by the virtue of our invention a positive pressure is created when an injector pushes the adipose tissue whereas a negative pressure is created when the other injector pulls the adipose tissue and therefore the adipose tissues are digested (they are split) without being damaged, by the vacuum effect created by the injector applying the negative pressure; because pushing movement crashes and crumbles the adipose tissues.

In the patent document with number WO2009073724, which sets another example for the prior art, a process for adipose tissue to pass though the filters by a positive pressure is described. In addition, the filters are not sharp and the said process is not completely isolated from the outer environment. Therefore, the process is performed in a medium in which the cells are in contact with air. This increases the risk of the cells losing their vitality, contamination and infection. In addition, in the said document, volumetric loss occurs during the transference of the adipose tissue when the filters are changed if we take both the remaining on the filters and the spilled tissues into the account.

As a result, due to the inconveniencies mentioned above and the insufficiency of the existing solutions regarding the issue, a kit is developed which enables obtaining adipose-based stem cells in a more practical manner and also performing this process in the medium which the adipose tissue is obtained.

AIM OF THE INVENTION

The present invention is related to kit for obtaining adipose tissue-based stem cells, which fulfills the requirements mentioned above, which eliminates all the disadvantages and which provides some additional advantages and to its production method.

Primary goal of the invention is to develop kit specifically in order to be used for, obtaining Adipose tissue-based stem cells, which enables the obtaining of stem cells without changing the medium in which the adipose tissue is taken from the preferred area of the individual, for instance without the need of transferring the cells to the laboratory.

Another aim of the invention is to develop a kit, specifically in order to be used for, obtaining Adipose tissue-based stem cells, which enables the transplantation of the cells to be obtained to the individual with no contact with air and which eliminates the infection and contamination risks.

Another aim of the invention is to develop a kit, specifically in order to be used for, obtaining Adipose tissue-based stem cells, which enables the transplantation of the cells to be obtained to the individual without the cells losing their vitality by the virtue of a closed system.

Another aim of the invention is to develop a kit, specifically in order to be used for, obtaining Adipose tissue-based stem cells, which enables an efficient obtainment of the stem cells without any volumetric loss.

Another aim of the invention is to develop a kit, which enables the obtainment of the stem cells by mechanic methods in which the human-based adipose tissue is not exposed to any chemical or biological enzyme.

Another aim of the invention is to develop a kit, specifically in order to be used for, obtaining Adipose tissue-based stem cells, which enables an efficient obtainment of the stem cells where the stem cells are not affected by pressure, by enabling only the adipose cells explode by the help of negative pressure.

Another aim of the invention is to develop a kit, specifically in order to be used for, obtaining Adipose tissue-based stem cells, which enables the usage of a practical kit with low cost.

The present invention is an adipose tissue splitting kit, in order to realize the abovementioned aims, which comprises at least one reservoir through which the entrance of the adipose tissues, which are used for obtainment of adipose tissue-based stem cells, is performed; which enables mechanical digestion of the said adipose tissue; characterized by comprising;

at least one first housing, which is located on the said reservoir, which fits into the inlet of at least one first injector which retains the adipose tissue and which enables the transmission of the adipose tissue inside the said injector, at least one second housing, which is located on the said reservoir in a perpendicular position to the said first housing and which enables the at least one second injector to be positioned outside the reservoir and in a perpendicular position to the reservoir, at least one third housing which is located on the said reservoir in a perpendicular position to the said second housing and which enables the at least one third injector to be positioned outside the reservoir and in a perpendicular position to the reservoir, at least one body which is fixed inside the reservoir by the pins that are located inside the said reservoir, at least one first inlet which is located on the said body and which enables the transmission of the adipose tissue to the passage which is located in the body by pushing of the first injector, in which the adipose tissue is located, by being positioned in a manner to be concentric with the first housing that is located in the reservoir, at least one passage which can rotate its own axis and which enables the circulation of the adipose tissue that is taken from the injectors between a desired inlet inside the body and another inlet which is positioned in a 90 degree angle to this inlet by this rotation movement and which lies as L shape inside the body, at least one cover which enables the said movement of the passage by being positioned in a manner to be connected to the passage shape on the body and covers the top of the reservoir, at least one second inlet which comprises at least one first splitting element,
which is located on the said body in a manner to be positioned perpendicular to the said first inlet,
which is positioned in a manner to be concentric with the second housing that is located in the reservoir and enables the adipose tissue split when it enters to and exits from the second injector by the virtue of the negative pressure the second injector creates, during the transmission of the adipose tissue from first injector to the second injector,
which is obtained by alignment of a multiple of cutting elements, at least one third inlet which comprises at least one second splitting element,
which is located on the said body in a manner to be positioned parallel to the said first inlet, and which is positioned in a manner to be concentric with the third housing which is located in the reservoir,
which enables the adipose tissue split when it enters to and exits from the third injector by the virtue of the negative pressure the third injector creates, during the transmission of the adipose tissue from second injector to the third injector,
which has cutting elements located closer to each other in comparison to the cutting elements that are in the said first splitting element.

In order to realize the aims of the invention, the invention comprises at least one body which is fixed inside the reservoir by the help of the pins that are located in the said reservoir and by the inlets being positioned concentrically inside the said housings, where there are empty spaces between the said inlets. By the housings, the injected adipose tissue is transmitted to the L-shaped passage that is located inside the close body. By this way, adipose tissues are taken into the kit without having a contact with the outer environment and the risks of infection, contamination etc. are eliminated.

In order to realize the aims of the invention, the present invention comprises at least one passage which can rotate its own axis and which enables the circulation of the adipose tissue, that is taken from the said first housing of the reservoir to the first inlet of the body, between a first inlet inside the body and a second inlet which is positioned in a 90 degree angle to this inlet by this rotation movement and which lies in an L shape inside the body. By the virtue of the said passage, the transmission of the adipose tissue to the injector applying negative pressure is performed and the circulation of the adipose tissue through the desired injectors on the kit is obtained.

In order to realize the aims of the invention, the present invention comprises at least one splitting element which enables the adipose tissue split when it enters to and exits from the injector by the virtue of the negative pressure the injector creates, during the transmission of the adipose tissue from one injector to another injector and which is obtained by alignment of a multiple of cutting elements and a second splitting element which has cutting elements located closer to each other in comparison to the cutting elements that are in the said first splitting element. In addition, it comprises at least one second splitting element which enables the adipose tissue split when it enters to and exits from the third injector by the virtue of the negative pressure the third injector which is located in the said third inlet, creates, during the transmission of the adipose tissue from second injector to the third injector and which is obtained by alignment of a multiple of cutting elements and which has cutting elements located closer to each other in comparison to the cutting elements that are in the said first splitting element. By this manner, stem cells are efficiently obtained from adipose cells, which are split by the first splitting element, without using an enzyme by the virtue of the second splitting element.

In order to realize the aims of the invention, the present invention comprises housings which are located on the said reservoir and fit to the inlet of the injector which retains the Adipose tissue and which enable the injector which retains the Adipose tissue be positioned outside the reservoir and in a perpendicular position to the reservoir. By the virtue of the said injectors being positioned in a perpendicular manner to the reservoir, an efficient negative pressure is created and all of the cells participate into the process being performed in the kit. In addition, by the help of the injectors in the kit, the adipose tissue is not being pushed inside the kit, but it is drawn by creation of a negative pressure. Therefore, the adipose molecules split by the vacuum effect and the regenerative stem cells are obtained in a pure condition.

In order to realize the aims of the invention, the kit of the present invention performs the obtainment of stems cells from the said tissues in a practical manner and in a medium which is not different than the medium in which the obtainment of adipose tissues from the patient is performed. Therefore the efficiency of the applied transplant process to the individual is increased without the adipose tissue-based stem cells lose their vitality.

The structural and characteristical features of the invention along with all its advantages shall be understood more clearly with the Figures provided below and the detailed description that refers to these figures. Therefore, an evaluation shall be made by taking these figures and the detailed description into account.

BRIEF DESCRIPTION OF DRAWINGS

It is not necessary that the figures are scaled and the details that are not required in order to understand the present invention may be ignored. In addition to that, elements which are majorly identical or which have majorly identical functions are shown with the same number.

DESCRIPTION OF THE PART REFERENCES

Figure 1:
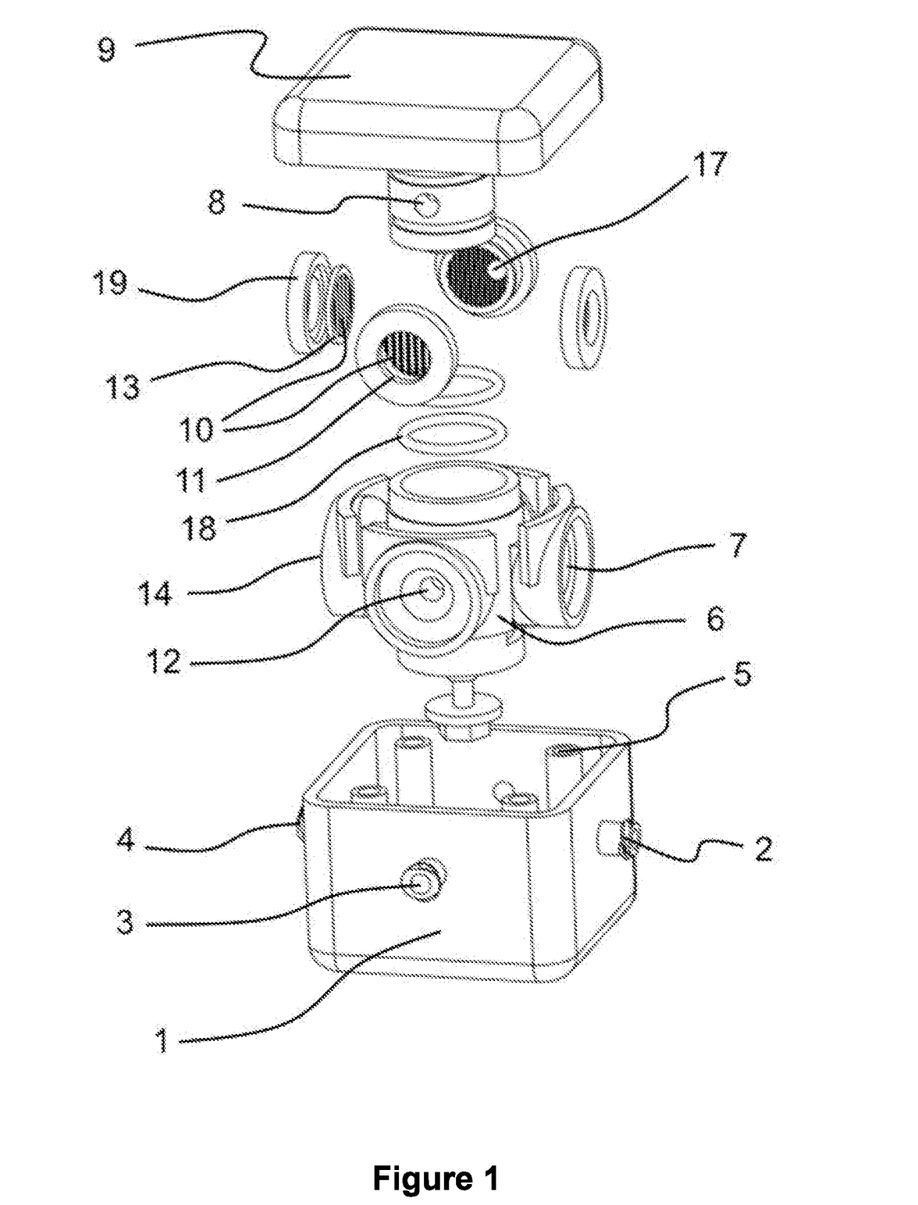
FIG. 1 Is an exploded perspective view of the kit that is developed by the present invention.
Figure 2:
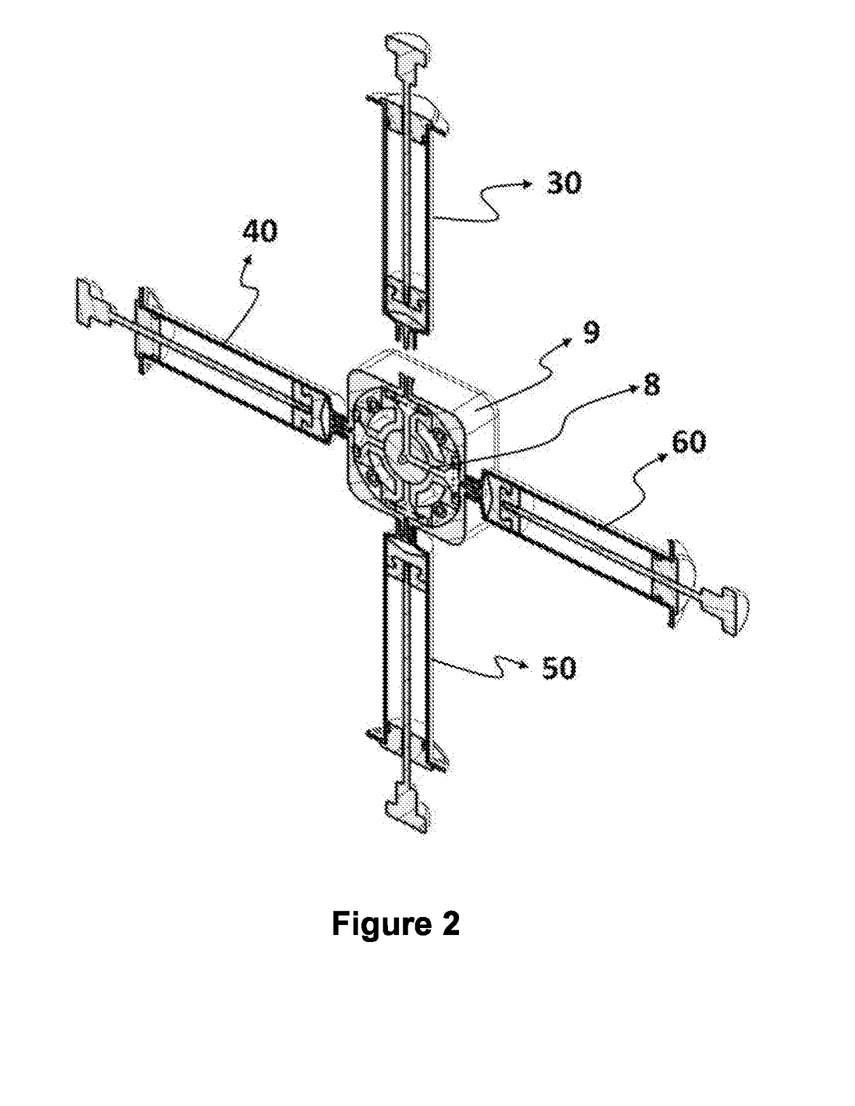
FIG. 2 Is a sectional view of the kit with the injectors, that is developed by the present invention.
Figure 3:
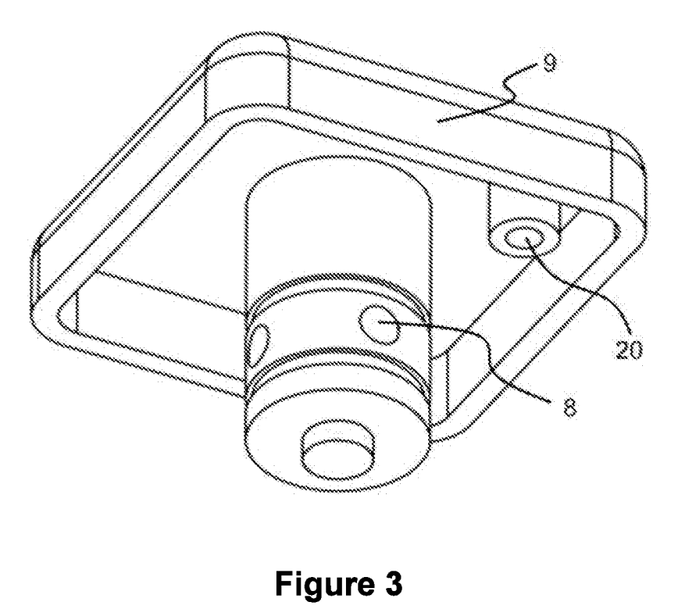
FIG. 3 Is a detailed view from bottom of the cover that is comprised in the kit, that is developed by the present invention.
Figure 4:
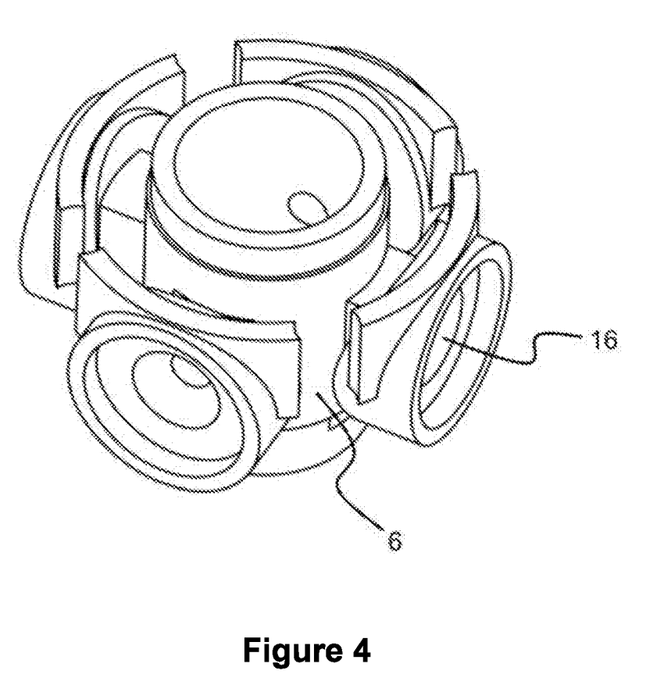
FIG. 4 Is a detailed perspective view of the body that is comprised in the kit, that is developed by the present invention FIG. 5 Is a detailed view from top of the reservoir that is comprised in the kit, that is developed by the present invention.
Figure 5:
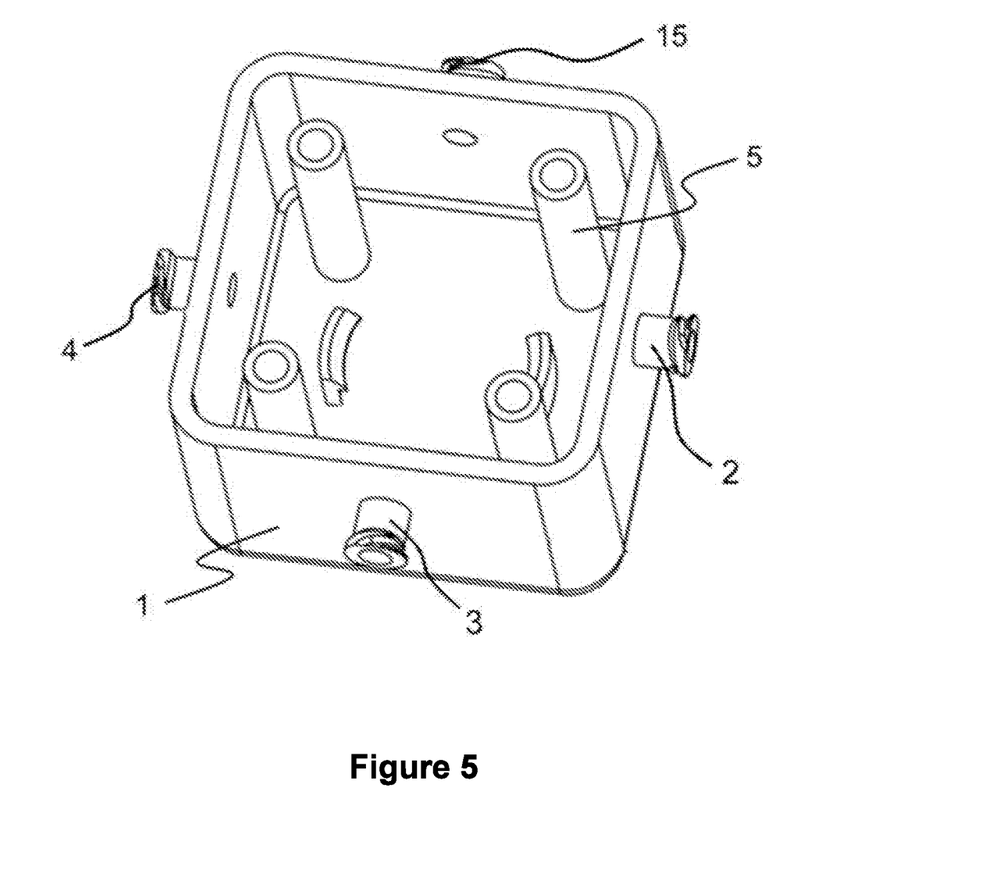

1. Reservoir
2. First housing
3. Second housing
4. Third housing
5. Pin
6. Body
7. First inlet
8. Passage
9. Cover
10. Cutting element
11. First splitting element
12. Second inlet
13. Second splitting element
14. Third inlet
15. Forth housing
16. Forth inlet
17. Third splitting element
18. First sealing ring
19. Second sealing ring
20. Orifice
30. First injector
40. Second injector
50. Third injector
60. Forth injector

DETAILED DESCRIPTION OF THE INVENTION

In this detailed description a kit of the invention that is developed for obtaining the Adipose tissue-based stem cells and its preferred structurings are described in order for the issue to be better understood and this description is not limiting in any manner.

In an example application of the lit which is realized with the present invention and is used for obtaining the Adipose tissue-based stem cells and comprises a reservoir (1), the first injector (30) which refrains the adipose tissue that is taken from a predetermined area of the individual is attached to a first housing (2) which is located on the said reservoir (1) and which is suitable for the inlet of the first injector (30) which refrains the adipose tissue. The adipose tissue which is retained by the First injector (30) is transmitted without the kit having any contact with air or outer environment. There is a third housing (4) which is positioned opposing with the said first housing (2) on the Reservoir (1) and which is positioned in a manner to be perpendicular to a second housing (3). An empty second injector (40) and the third injector (50) are attached to the said housings (3, 4) in a manner to be out of and perpendicular to the reservoir (1). A body (6) which comprises at least one first inlet (7) which enables the transmission of the adipose tissue into the passage (8) inside the body (6); by pushing the first injector (30), which is positioned inside the reservoir (1), in a manner to be concentric with the first housing (2) that is located in the reservoir (1), by the help of the pins (5) that are positioned inside the said reservoir (1) and which comprises the adipose tissue. There is a second inlet (12) comprised, which is positioned on the said body (6) in a manner to be perpendicular to the said first inlet (7) and to be concentric with the second housing (3) that is located on the reservoir (1); and a third inlet (14) which is positioned on the said body (6) in a manner to be perpendicular to the said first inlet (7) and to be concentric with the third housing (4) that is located on the reservoir (1). Because the said inlets are positioned concentrically with the housings, the second inlet (12) is connected to the second injector (40) while the third inlet (14) is connected to the third injector (50).

There is at least one forth housing (15) which is located on the said reservoir (1) in a manner to be perpendicular to the said first housing (2) and the third housing (4) and to be placed against the said second housing (3) and which enables at least one forth injector (60) to be positioned out of the reservoir (1) in a manner to be perpendicular to the reservoir (1). There is at least one forth inlet (16) which is located in the body (6) in a manner to be concentric with the said forth housing (15). There is a at least one third splitting element (17) comprised, which is located in the said forth inlet (16) and which has cutting elements (10) closer to each other in comparison to the cutting elements in the said second splitting element (13). By this way, the splitting process occurs more efficiently. The forth injector (60) which is located in the said forth housing (15), enables the Adipose tissue split during its entrance to and exit from the forth injector (60), due to the negative pressure it applies, during the transmission of the adipose tissue from third injector (50) to the forth injector (60). It is preferred that the number of the said splitting elements in the invention is at least two.

There is at least one passage (8) comprised, which lies in L shape inside the body (6), which can rotate on its own axis and which enables by this rotation movement the circulation of the adipose tissue inside it between a desired inlet (7, 12, 14, 16) inside the body (6) and another inlet (7, 12, 14, 16) which is positioned in a 90 degree angle to the said inlet. In the kit that is developed by the present invention, there is a cover (9) comprised which covers the top of the reservoir (1), which is connected to the passage (8) and which enables the passage (8) to rotate around its own axis in a manner to have a 90-degree-angle. Therefore, the said passage (8) can rotate in a manner to adjust the distance between itself and the inlets inside the body (6) as 90 degrees and rotates a full circle inside the body (6) and around its own axis. The injector is drawn by attaching the second injector (40) to the second housing (3) which is positioned on the reservoir (1) which corresponds to the second inlet (12) which is positioned in a 90 degree-angle with the said first inlet (7). Drawing of the said second injector (40) results in the creation of a negative pressure in the passage (8) and the adipose tissue passes from the said first inlet (7) to the second inlet (12). Adipose tissue passes through a first splitting element (11) which is located on the second inlet (12). By drawing and releasing of the said first injector (30) and the second injector (40), it is enabled that the adipose tissue passes through a first splitting element (11) which is located on the second inlet (12) multiple times. Therefore, the adipose tissue passing through the first splitting element (11) starts to split. By the rotation of the cover (9) that is located on the kit, the passage (8) performs the rotation movement of 90 degrees around its own axis in clockwise or counterclockwise direction. Therefore, it is enabled that a passing occurs between the said second inlet (12) and a third inlet (14) that is perpendicular to it. By the virtue of at least one second splitting element (13) which is located on the said third inlet (14) and which has cutting elements (10) located closer to each other in comparison to the cutting elements (10) that are in the said first splitting element (11); by the help of the negative pressure created by the third injector (50), the adipose tissue is transmitted from the second injector (40) to the third injector (50). Therefore, the adipose tissue passes through the said second splitting element (13) and splits. By the developed kit, the adipose tissue is not being pushed inside the kit, but it is drawn by creation of a negative pressure. Therefore, the adipose molecules split by the vacuum effect and by the splitting elements; and the regenerative stem cells are obtained in a pure condition.

The said adipose cells are loaded into an injector by the rotation of the passage (8) and the cover (9) which are located on the kit. The process is completed by drawing the adipose cells into the first injector (30). Therefore, the adipose tissue, which is loaded into the reservoir (1) without any contact with air, is split by passing through all the said splitting elements (11, 13) by the rotation movement of the cover (9) and the freed stem cells are taken without any contact with air after isolation and are sent to centrifuge in order to be transplanted to the patient A preferred implementation of the invention comprises at least one first sealing ring (18) which provides impermeability in order to prevent adipose tissue to leak from the space that occurs when the said cover (9) enters into the body (6).

Another preferred implementation of the invention comprises at least one second sealing ring (19) which enables the cutting blades seat onto the body (6).

A preferred implementation of the invention comprises at least one orifice (20) that is located in the cover (9). By the said orifice (20), body (6) seats onto the reservoir (1) well and it is enabled that the passage (8) inside the body (6) easily rotates with the desired 90 degree angle.

By virtue of the kit that is developed by the present invention, adipose tissue-based stem cells can be obtained without using any enzymes. The said adipose cells are loaded into an injector which is made of a metal suitable to be used in centrifuge, by the rotation of the passage (8) and the cover (9) which are located on the kit. The process is completed by drawing the adipose tissue-based stem cells into the said injector. Therefore, the adipose tissue, which is loaded into the reservoir (1) without any contact with air, is split by passing through all the said splitting elements (11, 13, 17) by the rotation movement of the cover (9) and the obtained stem cells are taken without any contact with air and are sent to centrifuge in order to be transplanted to the patient.

What is claimed is:

1. An adipose tissue splitting kit comprising at least one reservoir, wherein an entrance of adipose tissues used in an obtainment of adipose tissue-based stem cells through the at least one reservoir, and the adipose tissue splitting kit enables a mechanical digestion of an adipose tissue, wherein the adipose tissue splitting kit comprising:
   at least one first housing located on the at least one reservoir, wherein the at least one first housing fits into at least one first inlet of at least one first injector retaining the adipose tissue and the at least one first housing enables a transmission of the adipose tissue inside the at least one first injector;
   at least one second housing located on the at least one reservoir in a perpendicular position to the at least one first housing and the at least one second housing enables at least one second injector to be positioned outside the at least one reservoir and in a perpendicular position to the at least one reservoir;
   at least one third housing located on the at least one reservoir in a perpendicular position to the at least one second housing and the at least one third housing enables at least one third injector to be positioned outside the at least one reservoir and in a perpendicular position to the at least one reservoir;
   at least one body fixed inside the at least one reservoir by pins, wherein the pins are located inside the at least one reservoir;
   the at least one first inlet located on the at least one body and the at least one body enables the transmission of the adipose tissue to a passage located in the at least one body by pushing of the at least one first injector, wherein in the at least one first injector the adipose tissue is located, by being positioned to be concentric with the at least one first housing that is located in the at least one reservoir;
   wherein the passage comprises an axis and is configured to rotate about the axis and the passage enables a circulation of the adipose tissue taken from the at least one first injector and the at least one second injector between the at least one first inlet inside the at least one body and at least one second inlet positioned in a 90 degree angle to the at least one first inlet by a rotation movement and the passage lies as an L shape inside the at least one body;
   at least one cover enabling the rotation movement of the passage by being positioned to be connected to a passage shape on the at least one body and the at least one cover covers a top of the at least one reservoir;

the at least one second inlet comprising at least one first splitting element; and the at least one second inlet is located on the at least one body to be positioned perpendicular to the at least one first inlet;

the at least one second inlet is positioned to be concentric with the at least one second housing located in the at least one reservoir and the at least one second inlet enables an adipose tissue split when the adipose tissue split enters to and exits from the at least one second injector by a virtue of a negative pressure the at least one second injector creates, during the transmission of the adipose tissue from the at least one first injector to the at least one second injector; and the at least one second inlet is obtained by an alignment of a plurality of cutting elements;

at least one third inlet comprising at least one second splitting element; wherein the at least one third inlet is located on the at least one body to be positioned parallel to the at least one first inlet, and the at least one third inlet is positioned to be concentric with the at least one third housing located in the at least one reservoir;

the at least one third inlet enables the adipose tissue split when the adipose tissue enters to and exits from the at least one third injector by the virtue of the negative pressure the at least one third injector creates, during the transmission of the adipose tissue from the at least one second injector to the at least one third injector.

2. The adipose tissue splitting kit according to claim 1, comprising at least one fourth housing located on the at least one reservoir to be positioned perpendicular to the at least one first housing and the at least one third housing and the at least one fourth housing enables at least one empty injector be positioned outside the at least one reservoir and in a perpendicular position to the at least one reservoir.

3. The adipose tissue splitting kit according to claim 2, comprising at least one fourth inlet positioned on the at least one body to be concentric with the at least one fourth housing.

4. The adipose tissue splitting kit according to claim 3, comprising at least one third splitting element located on the at least one fourth inlet.

5. The adipose tissue splitting kit according to claim 1, comprising at least one first sealing ring, wherein the at least one first sealing ring provides impermeability for the adipose tissue not to leak when the at least one cover gets into the at least one body.

6. The adipose tissue splitting kit according to claim 5, comprising at least one second sealing ring, wherein the at least one second sealing ring enables the plurality of cutting elements position on the at least one body.

7. The adipose tissue splitting kit according to claim 1, comprising at least one orifice positioned on the at least one cover, wherein the at least one orifice enables the at least one cover to seat on the at least one reservoir.

8. The adipose tissue splitting kit according to claim 1, wherein the at least one reservoir has a cubic form.

9. The adipose tissue splitting kit according to claim 1, comprising four pieces of injectors made of metal, wherein the adipose tissue-based stem cells are loaded into the four pieces of injectors and the four pieces of injectors are suitable to be used in a centrifuge.

\* \* \* \* \*